US007825064B2

(12) United States Patent
Wong et al.

(10) Patent No.: US 7,825,064 B2
(45) Date of Patent: Nov. 2, 2010

(54) SUPPORTED CATALYSTS USING NANOPARTICLES AS THE SUPPORT MATERIAL

(75) Inventors: Michael S. Wong, Houston, TX (US);
Israel E. Wachs, Bethlehem, PA (US);
William V. Knowles, Pearland, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 10/558,917

(22) PCT Filed: Jun. 3, 2004

(86) PCT No.: PCT/US2004/017498

§ 371 (c)(1),
(2), (4) Date: Aug. 29, 2006

(87) PCT Pub. No.: WO2005/002714

PCT Pub. Date: Jan. 13, 2005

(65) Prior Publication Data

US 2007/0009417 A1    Jan. 11, 2007

Related U.S. Application Data

(60) Provisional application No. 60/475,556, filed on Jun. 3, 2003.

(51) Int. Cl.
| | |
|---|---|
| *B01J 23/00* | (2006.01) |
| *B01J 23/32* | (2006.01) |
| *B01J 23/46* | (2006.01) |
| *B01J 23/40* | (2006.01) |
| *B01J 23/70* | (2006.01) |
| *B01J 23/745* | (2006.01) |
| *B01J 23/75* | (2006.01) |

(52) U.S. Cl. .............. 502/305; 502/311; 502/312; 502/313; 502/316; 502/321; 502/324; 502/325; 502/326; 502/338; 502/353

(58) Field of Classification Search ................ 502/305, 502/311–313, 316, 321, 324–326, 338, 353
See application file for complete search history.

(56) References Cited

U.S. PATENT DOCUMENTS 3,284,369 A    11/1966   Bergna et al.

(Continued)

FOREIGN PATENT DOCUMENTS

DE          19951781 A1    5/2001

(Continued)

OTHER PUBLICATIONS

Soler-Illia et al., Design of meso-structured titanium oxo hybrid organic-inorganic networks, New J. Chem., 2001, 25, p. 156-165.*

(Continued)

*Primary Examiner*—David M. Brunsman
*Assistant Examiner*—Kevin M Johnson
(74) *Attorney, Agent, or Firm*—Conley Rose, P.C.; Rodney B. Carroll

(57) ABSTRACT

A process for making a porous catalyst, comprises a) providing an aqueous solution containing a nanoparticle precursor, b) forming a composition containing nanoparticles, c) adding a first catalytic component or precursor thereof and a pore-forming agent to the composition containing nanoparticles and allowing the first catalytic component, the pore-forming agent, and the nanoparticles form an organic-inorganic structure, d) removing water from the organic-inorganic structure; and e) removing the pore-forming agent from the organic-inorganic structure so as to yield a porous catalyst.

22 Claims, 1 Drawing Sheet

U.S. PATENT DOCUMENTS

| | | | |
|---|---|---|---|
| 3,907,921 A * | 9/1975 | Winter, III | 585/660 |
| 4,257,874 A | 3/1981 | Bergna | |
| 5,098,684 A | 3/1992 | Kresge et al. | |
| 5,439,865 A * | 8/1995 | Abe et al. | 502/333 |
| 5,622,684 A | 4/1997 | Pinnavaia et al. | |
| 5,840,111 A | 11/1998 | Wiederhoft et al. | |
| 5,879,715 A | 3/1999 | Higgins et al. | |
| 5,958,367 A * | 9/1999 | Ying et al. | 423/701 |
| 6,074,979 A | 6/2000 | Hagemeyer et al. | |
| 6,090,746 A | 7/2000 | Bonnemann et al. | |
| 6,391,818 B1 | 5/2002 | Bonsel et al. | |
| 6,548,440 B1 | 4/2003 | Pham et al. | |
| 6,569,358 B1 * | 5/2003 | Tai et al. | 252/512 |
| 6,603,038 B1 | 8/2003 | Hagemeyer et al. | |
| 6,686,308 B2 | 2/2004 | Mao et al. | |
| 7,005,118 B2 | 2/2006 | Terres Rojas et al. | |
| 2003/0069131 A1 | 4/2003 | Ying et al. | |

FOREIGN PATENT DOCUMENTS

| | | |
|---|---|---|
| EP | 0266011 A1 | 5/1988 |
| EP | 1293479 A1 | 3/2003 |
| EP | 1422198 A1 | 5/2004 |
| WO | 0132558 A1 | 5/2001 |
| WO | 02057183 A1 | 7/2002 |
| WO | 02057184 A1 | 7/2002 |
| WO | 03004412 A1 | 1/2003 |
| WO | 03011762 A1 | 2/2003 |
| WO | 2006119550 A1 | 11/2006 |

OTHER PUBLICATIONS

Edler et al., Room-temperature Formation of Molecular Sieve MCM-41, J. Chem. Soc., Chem. Commun., 1995, p. 155-156.*

Brinker et al., Evaporation-Induced Self-Assembly: Nanostructures Made Easy, 1999, Advanced Materials, 11, No. 7, p. 579-585.*

Hwang, Young Kyu et al., Nanoparticle routes to mesoporous titania thin films, 2001, Chem. Commun., pp. 1738-1739.*

Wong, Jeng, and Ying, *Supramolecular Templating of Thermally Stable Crystalline Mesoporous Metal Oxides Using Nanoparticulate Precursors*, 2001 American Chemical Society Nano Letters vol. 1, No. 11 (pp. 637-642).

Foreign communication from a related counterpart application—Supplementary European Search Report, EP 04776251.3, Sep. 29, 2009, 10 pages.

Gao, Xingtao, et al., "Structural and reactivity properties of Nb—MCM-41: comparison with that of highly dispersed Nb2O5/SiO2 catalysts," XP-002545355, Journal of Catalysis, 2001, pp. 18-24, vol. 203, Academic Press.

Huo, Qisheng, et al., "Generalized synthesis of periodic surfactant/inorganic composite materials," XP 000573990, Letters to Nature, Mar. 24, 1994, pp. 317-321, vol. 368, Nature.

Huo, Qisheng, et al., "Organization of organic molecules with inorganic molecular species into nanocomposite biphase arrays," XP 000573966, Chem. Mater., 1994, pp. 1176-1191, vol. 6, No. 8, American Chemical Society.

Knowles, William V., et al., "Supported metal oxides and the surface density metric," XP-002545362, undated but included on Supplemental European Search Report for related counterpart application EP 04776251.3, pp. 251-281.

Kresge, C. T., et al., "Ordered mesoporous molecular sieves synthesized by a liquid-crystal template mechanism," XP 000573992, Letters to Nature, Oct. 22, 1992, pp. 710-712, vol. 359, Nature.

Liu, Yu, et al., "Aluminosilicate nanoparticles for catalytic hydrocarbon cracking," XP-002545357, J. Am. Chem. Soc., 2003, pp. 2376-2377, vol. 125, No. 9, American Chemical Society.

Murray, C. B., et al., "Self-organization of CdSe nanocrystallites into three-dimensional quantum dot superlattices," XP-002545356, Nov. 24, 1995, pp. 1335-1338, vol. 270, Science.

Tanev, Peter T., et al., "Nanoporous materials," XP-002545360, Chapter 8 of "Chemistry of advanced materials: an overview," edited by Leonard V. Interrante, et al., 1998, pp. 329-388, Wiley-VCH, Inc.

Wong, Michael S., et al., "Supramolecular-templated synthesis of nanoporous zirconia—silica catalysts," XP-001162203, Chem. Mater., 2002, pp. 1961-1973, vol. 14, No. 5, American Chemical Society.

Wong, Michael S., et al., "Surfactant-templated mesostructured materials: synthesis and compositional control," XP-002545361, undated but included on Supplemental European Search Report for related counterpart application EP 04776251.3, pp. 125-164.

Yada, Mitsunori, et al., "Mesoporous magnetic materials based on rare earth oxides," XP-002545358, Angew. Chem. Int. Ed., 1999, pp. 3506-3510, vol. 38, No. 23, Wiley-VCH Verlag GmbH, D-69451 Weinheim.

Yang, Peidong, et al., "Block copolymer templating syntheses of mesoporous metal oxides with large ordering lengths and semicrystalline framework," XP-002162652, Chem. Mater., 1999, pp. 2813-2826, vol. 11, No. 10, American Chemical Society.

Ying, Jackie Y., et al., "Synthesis and applications of supramolecular-templated mesoporous materials," XP-002545354, Angew. Chem. Int. Ed., 1999, pp. 57-77, vol. 38, Wiley-VCH Verlag GmbH, D-69451 Weinheim.

Zarur, Andrey J., et al., "Reverse microemulsion synthesis of nanostructured complex oxides for catalytic combustion," XP-002545359, Letters to Nature, Jan. 6, 2000, pp. 65-67, vol. 403, Nature, Macmillan Magazines Ltd.

* cited by examiner

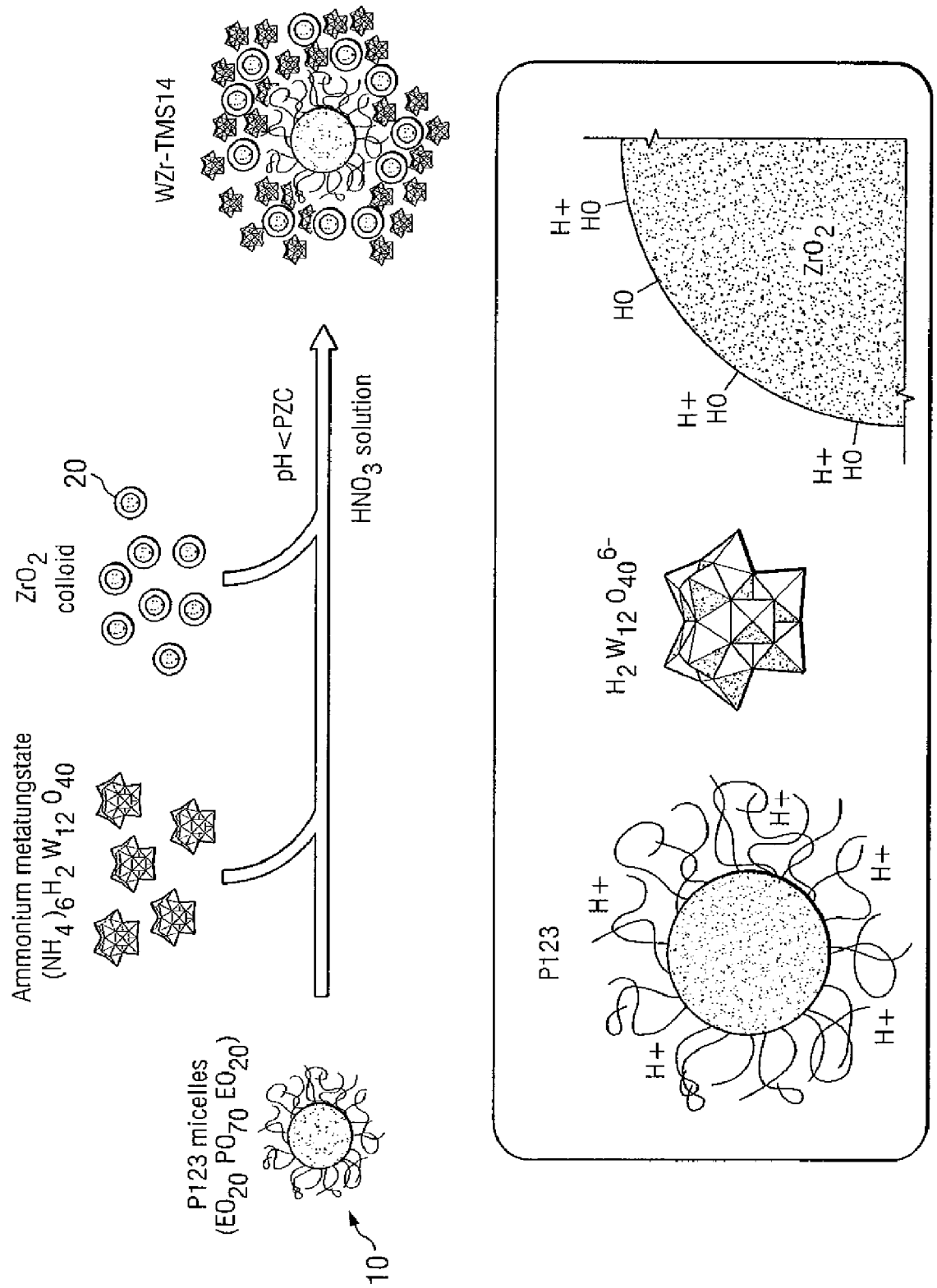

SUPPORTED CATALYSTS USING NANOPARTICLES AS THE SUPPORT MATERIAL

STATEMENT REGARDING FEDERALLY SPONSORED RESEARCH OR DEVELOPMENT

This invention was made with government support under grant number DE-FG02-93ER14350 awarded by the U.S. Department of Energy. The government has certain rights in the invention.

FIELD OF THE INVENTION

The present invention relates generally to catalytic materials and more particularly to catalysts composed of metal oxide on which is supported another metal oxide. The support comprises nanometer-sized metal oxide particles.

BACKGROUND OF THE INVENTION

Supported metal oxide catalysts are one of the major forms of materials used as heterogeneous catalysts. They are composed of an active material deposited on the surface of a high-surface area support, which the nominal purpose of achieving high dispersion of the active material. However, the support material may contribute to catalysis also, by providing or generating new active sites. With compositions spanning across the Periodic Table, supported metal oxide catalysts are found in industrial chemical processes, commercial applications, and environmental protection, such as automobile catalytic converters, NOx reduction from power plants, petroleum refining, drug manufacture, and petrochemicals processing.

The preparation method for these catalysts typically involves soaking the support metal oxide in a solution containing the solubilized precursors of the metal oxide to be supported. Drying causes the precursor to adsorb on the surface of the support metal oxide and calcination at high temperatures converts it to a metal oxide. This impregnation method ensures the active phase is exposed on the support surface and is commonly used to prepared commercial catalysts. This method has several drawbacks, namely: the amount of active phase that can be supported is relatively low (compared to precipitation, the other common method to industrial catalysts); the distribution of active phase throughout the catalyst may not be uniform; and the support material is typically composed of a random microstructure. Hence it is desired to provide a catalyst that avoids the shortcomings of the prior art.

SUMMARY OF THE INVENTION

The present invention features mesoporous metalated metal oxides, in which one meal oxide is the active phase and the support comprises metal oxide nanoparticles. Catalysts in accordance with the present invention show good distribution of the active phase and enhanced catalytic activity. Techniques useful for preparing catalysts in accordance with the present invention are known and are disclosed in M. S. Wong, E. S. Jeng, and J. Y. Ying, "Supramolecular Templating of Thermally Stable Crystalline Mesoporous Metal Oxides Using Nanoparticulate Precursors," Nano Lett. 1, 637-642 (2001, which is incorporated herein by reference.

In certain embodiments, a colloidal suspension of ZrO2 nanoparticles is combined with a surfactant solution and a metatungstate anion solution, forming an organic-inorganic mesostructured material. After the surfactant is removed through calcination, a mesoporous tungstated zirconia is formed (named WZr-TMS14). WZr-TMS14, or nano-WO3/ZrO2, has been found to be ~7 times more active (per active site on the catalyst) than the conventional material for methanol oxidation, even after accounting for the higher surface area and greater WO3 content of nano-WO3/ZrO2. In other embodiments, the tungsten is replaced with vanadium, zirconium, or other metal and/or the zirconia is replaced with titania, alumina, or other metal oxide.

The present nanoparticle-based supported metal oxide catalysts could replace conventional catalysts in industrial chemical processes, commercial applications, and environmental protection, such as automobile catalytic converters, NOx reduction from power plants, petroleum refining, drug manufacture, and petrochemicals processing. They could be also used as additives in the above applications.

The present compositions and methods provide a combination of features and advantages that overcome various problems of prior catalytic systems. The various characteristics described above, as well as other features, will be readily apparent to those skilled in the art upon reading the following detailed description of the preferred embodiments of the invention, and by referring to the accompanying drawing.

BRIEF DESCRIPTION OF THE DRAWINGS

For a more detailed description of the preferred embodiment of the present invention, reference will now be made to the accompanying drawing, which is a schematic diagram illustrating a possible mechanism for the self-assembly of the present catalysts.

DETAILED DESCRIPTION OF THE PREFERRED EMBODIMENT

The present invention comprises a highly effective catalyst system and methods for making same. In preferred embodiments, a metal oxide precursor is mixed with nanoparticles of a metal oxide support in a solution that contains a surfactant. The surfactant serves as a template for the metal oxide particles, which in turn support a self-assembled layer of the precursor salt species to the desired metal oxide layer. Referring briefly to the FIGURE, micelles of surfactant 10 are each surrounded by a plurality of metal oxide nanoparticles 20. Nanoparticles 20 are surrounded by the metal salt precursor. Once the nanoparticles, metal salt precursor, and surfactant have self-assembled, calcination converts the salt species into a metal oxide layer and removes the surfactant to leave a porous structure.

In certain embodiments, catalysts are made by combining the various components or precursors thereof in an aqueous solution. In the initial contacting step, an amount of a salt of the desired metal oxide is added to an aqueous solution containing a surfactant. After mixing, a colloidal sol of nanoparticles of the desired support is added to the mixture. The weight ratios of the ingredients in the resulting mixture are preferably in the range of 0.25-5.0 nanoparticles of desired support: 0.1-5.0 oxide of desired active metal: 0.1 to 5 surfactant: 5-25 water. More preferred weight ratios of the ingredients in the resulting mixture are in the range of 0.5-2.0 nanoparticles of desired support: 0.2-1.0 oxide of desired active metal: 0.2 to 1 surfactant: 10-15 water. The weight ratios in an exemplary mixture for making WZr-TMS14 can be 1.0 $ZrO_2$: 0.5 $(NH_4)_6H_2W_{12}O_{40}$: 0.5 surfactant: 11.9 $H_2O$.

The supramolecular templating synthesis of catalyst systems is believed to entail the cooperative electrostatic and hydrogen bonding interactions among the three components in order for self-assembly to occur. The three components are known to assume a charge in solution under the low pH conditions used. The colloidal metal oxide particle surfaces are positively charged when the synthesis pH (~0.5) is below the point of zero charge (pzc) for that metal oxide. For example, $pzc_{zirconia}$=4-6. The active metal species, e.g. metatungstate, is a negatively-charged molecular cluster at low to neutral pHs. In fact, low pHs favor the formation of metatungstate and other isopolytungstates. Likewise, triblock copolymer surfactant micelles are postulated to carry a positive charge via hydrogen bonding of the poly(ethylene oxide) corona (surrounding the poly(propylene oxide) core) with hydrated protons, in a manner similar to polyethylene glycol.

By way of example, the formation of WZr-TMS14 can be described through a $(S^oH^+)(I^-C^+)$ pathway, in which $S^o$ represents the nonionic surfactant; $H^+$, the proton; $I^-$, the metatungstate; and $C^+$, the inorganic colloid. Through attractive electrostatic interactions, the metatungstate species bind to the surfaces of both hydrogen-bonded micelle and zirconia colloid moieties to form WZr-TMS 14, as shown in the FIGURE. It has been discovered that WZr-TMS14 and the other compounds described herein differ from previously known compounds in two ways: the inorganic anion is incorporated into the material and the metal oxide precursor is colloidal in nature.

Variations

The surfactant can be any ethylene oxide polymer, and is preferably selected from the group of block copolymers. Suitable polymer surfactants include but are not limited to nonionic poly(ethylene oxide)-poly(propylene oxide)-poly(ethylene oxide) triblock copolymer with the structural formula $EO_{20}PO_{70}EO_{20}$, where EO represents ethylene oxide ($-CH_2-CH_2-O-$) and PO represents linear propylene oxide ($-CH_2-CH_2-CH_2-O-$) chains, with a molecular weight of ~5750, sold under the trademark Pluronic® P123 by BASF,; $EO_5PO_{70}EO_5$ with a molecular weight of ~440; $EO_{106}PO_{70}EO_{106}$ with a molecular weight of ~12600, and $EO_{17}PO_{60}EO_{17}$ with a molecular weight of ~4950. Other suitable catalysts include positively charged surfactants such as hexadecyl trimethyl ammonium or the bromide thereof cetyl trimethyl ammonium bromide (CTAB). When these surfactants are used, it is preferred that the initial solution has a higher surfactant concentration than that of $EO_xPO_yEO_z$ surfactants. In addition it is preferred that the solution temperature be maintained above ambient but below boiling preferably in the range of 20-80° C. and more preferably in the range of 40-80° C.

It was found that the pore size of the final composition could be controlled by varying the size of the surfactant molecules and the relative sizes of the hydrophilic PEO and hydrophobic PPO blocks. For example, for a given surfactant MW, greater hydrophobicity favors formation of a mesoporous material with a higher surface area. Likewise, for a given hyrophobicity, surfactants with higher MWs lead to materials with higher surface areas and larger pore sizes. Polymers that have high MWs and are highly hydrophilic result in nonporous materials.

The tungsten can be replaced with any desired catalytically active metal, including but not limited to vanadium, niobium, tantalum, rhenium, rhodium, rubidium, cobalt, iron, manganese, and molybdenum (oxides including $WO_3$, $V_2O_5$, $Nb_2O_5$, $Ta_2O5$, $ReO_2$, $MoO_3$), any of which can used alone or in combination with one or more of the others. In addition, metal non-oxides, such as CdS, can be used.

Similarly, the zirconia nanoparticles can be replaced with titania, alumina, cesia, antimony hafnia, or silica ($TiO_2$, $Al_2O_3$, $CeO_2$, $HfO_2$, $Sb_2O_5$, $SiO_2$), each of which can be used alone or in combination with one or more of the others. The nanoparticles can comprise a substantially pure metal oxide, or can be a blend of metal oxides. Blends of nanoparticles having differing compositions may also be used. Further variations in the support can include metal non-oxide nanoparticles, e.g., CdSe quantum dots, nanoparticles of different sizes, and nanoparticles of different shapes.

The support metal(s) can be introduced as a solution of the desired metal oxide salt, or as a metal oxide precursor, such as a nitrate or chloride. If a colloidal sol of nanoparticles of the desired metal oxide is used, it is preferred that the nanoparticles be between 2 and 20 nm in diameter, more preferably between 2 and 10, and still more preferably between 5 and 10 nm in diameter. Colloidal sols of such particles are commercially available.

While one embodiment of the present invention is described above, in which the catalyst system is formed in an aqueous solution, alternate embodiments can also be used. For example, sol-gel processing, described in detail below, achieves a similar result while avoiding the precipitation regime.

The present methods appear to allow formation of a layer of metal oxide that is amorphous, rather than microcrystalline, despite having a surface density greater than the monolayer value. For example, tungsten oxide can be conceptualized as an overlayer on the zirconia nanoparticles, which is substantiated by the higher W/Zr-atomic ratio of the surface (1.44) than of the bulk (0.23). The surface density of tungsten oxide on zirconia was determined to be 6.0 $WO_3/nm^2$ (or ~10.0 $\mu mol/m^2$) from the measured tungsten oxide loading (30.5 wt %) and the overall surface area (130 $m^2/g$). A surface density of 4.0 $WO_3/n^2$ (6.6 $\mu mol/m^2$) has been reported to correspond to monolayer coverage of tungsten oxide on a zirconia support, based on laser Raman spectroscopy studies and gas titration experiments. A surface density in excess of the monolayer value should lead to the formation of $WO_3$ microcrystals on a variety of metal oxide supports, but no such phase segregation was found in WZr-TMS14. The higher observed surface tungsten oxide density is consistent with the more extensively polymerized surface tungsten oxide species observed with in situ Raman spectroscopy.

This overlayer model can be explored further by examining the surface area and tungsten oxide loading dependence on zirconia colloid size, assuming a spherical morphology for the zirconia particles. Using modeling based on surface area and density, a particle size of 5 nm was predicted to lead to a material with a surface area of ~130 $m^2/g$ and a $WO_3$ content of ~30 wt %. These values are similar to the measured values for 600° C.-calcined WZr-TMS14. Thus, WZr-TMSI4 can be described accurately as a mesoporous framework comprising 5-nm zirconia colloid particles coated with tungsten oxide.

It is known that the metal oxide layer is in the form of polymerized species, as detected through Raman spectroscopy. Generally, conventional metal oxides have only a small amount of this polymerized species. It is reasoned that the higher activities exhibited by the are the result of fewer microcrystallites in the catalytically active material.

EXAMPLES

Synthesis of Nano-$WO_3/ZrO_2$ Using Surfactant Templating

The synthesis of mesoporous tungstated zirconia designated WZr-TMS14 was described previously [15]. Briefly, ammonium metatungstate (($NH_4$)$_6$$H_2$$W_{12}$$O_{40}$ or "AWO", Strem) was added to a solution of Pluronic® P123 surfactant (MW-5750, BASF). This surfactant is a non-ionic poly(ethylene oxide)-poly(propylene oxide)-poly(ethylene oxide) triblock copolymer with the structural formula $EO_{24}PO_{70}EO_{20}$. A colloidal sol of zirconium oxide (Nyacol® Zr10/20, 20 wt % $ZrO_2$, PQ Corp.) was added to the stirring solution, and immediate precipitation resulted. The final weight ratio of the synthesis mixture was 1.0 $ZrO_2$:0.5 AWO:0.5 Pluronic:11.9 $H_2O$. After stirring for 2 hr, the mixture was left to age for 2 days at room temperature. A white precipitate was recovered, washed three times, and left to dry in air. After being ground into a fine powder, the sample was calcined under flowing air at 600° C. for 3 hr.

Pluronic triblock copolymer surfactants of different chain lengths were also used as templating agents: L121 ($EO_5PO_{70}EO_5$; MW ~4400), F127 ($EO_{106}PO_{70}EO_{106}$; MW ~12600), P84 ($EO_{20}PO_{39}EO_{20}$; MW ~4200), F87 ($EO_{63}PO_{39}EO_{63}$; MW ~7700), and P103 ($EO_{17}PO_{60}EO_{17}$; MW ~4950). The same weight amount of templating agent was used for all syntheses. Some dependence on the surfactants' molecular weight (MW) and hydrophile-lypophile balance (HLB) values was noted in the WZr-TMS14 materials. Supramolecular templating was not successful using surfactant molecules with molecular weights ≧7700 and HLB values ≧22. The molecular weight, surface area, and pore sizes are give in Table 1 below.

Other zirconium oxide precursors were also employed to form the framework: zirconyl nitrate and zirconium chloride. The zirconium salts were introduced as 0.02 M solutions. The equivalent weight of metal oxide was used.

The resulting WZr-TMS14 had a highly porous structure, with a BET surface area of ~130 $m^2/g$. The unevenly-shaped pores appeared to be interconnected and to have a wormlike characteristic. The irregularly-shaped pore openings were 3-6 nm in diameter, consistent with the BJH pore size distribution (centered at 4.0 nm) calculated from the adsorption branch of the Type IV nitrogen adsorption isotherm (Table 1). The pore walls of WZr-TMS14 measured 4-6 nm in thickness and contained crystalline grains of zirconia The SAED pattern of WZr-TMS14 was similar to that of cubic zirconia nanoparticles, but the rings were more diffuse.

TABLE 1

Surface areas and pore sizes of 600° C.-calcined WZr-TMS 14 prepared with different triblock copolymer templates.

| Surfactant template | Average MW (g/mol) | HEB | BET surface area ($m^2/g$) | Average pore size (nm) |
|---|---|---|---|---|
| $EO_5PO_{70}EO_5$ (L121) | 4400 | 1 | 109 | 6.5 |
| $EO_{20}PO_{70}EO_{20}$ (P123) | 5750 | 8 | 130 | 4.0 |
| $EO_{106}PO_{70}EO_{106}$ (F127) | 12600 | 22 | 1 | — |
| $EO_{17}PO_{60}EO_{17}$ (P103) | 4950 | 9 | 59 | 3.5 |
| $EO_{20}PO_{39}EO_{20}$ (P84) | 4200 | 14 | 14 | 2.0 |
| $EO_{63}PO_{39}EO_{63}$ (F87) | 7700 | 24 | 3 | — |

Synthesis of Nano-$TiO_2$/$ZrO_2$ and $Al_2O_3$/$ZrO_2$ Using Surfactant Templating The preparation of mesoporous tungstated titania (WTi-TMS14) and tungstated alumina (WA1-TMS14) followed the synthesis method for WZr-TMS14 except that colloidal $TiO_2$ and $Al_2O_3$ were prepared and used. A solution of 2.1 M $Ti^{4+}$ was prepared by adding 10 ml of $TiCl_4$ to 43.6 ml of water at 0° C. under flowing argon. Aliquots of this stock solution were diluted to 0.44 M $Ti^{4+}$ with deionized water or with KOH solutions of varying concentrations (0.5, 1.0 and 1.5 M) Just before use. A 0.45 M $Al^{3+}$ solution was obtained with $AlCl_3.6H_2O$ and NaOH addition at a NaOH/$Al^{3+}$ molar ratio of 2.2. The solution became cloudy immediately, but cleared up after 10 days of stirring at room temperature to form a colloidal sol of $[AlO_4Al_{12}(OH)_{24}(H_2O)_{12}]^{7+}$ ("$Al_{13}$") polycations. The equivalent weight of metal oxide was also used. The physical properties of the resulting materials are given in Tables 2 and 3 below.

TABLE 2

Physical properties of WTi-TMS14 prepared with different KOH solution concentrations.

| KOH Concentration (M) | Bragg spacing (mu) Uncalcined | Bragg spacing (mu) Calcined | Surface area $m^2/g$ | Grain size (nm)[a] | Pore size (nm) |
|---|---|---|---|---|---|
| 0.0 | 8.3 | — | <1 | — | — |
| 0.5 | 10.3 | — | 2 | <1.4 | — |
| 1.0 | 10.8 | 9.8 | 15 | <1.4 | 4.4 |
| 1.5 | 10.8 | 9.8 | 126 | 1.4 | 3.9 |
| 1.5 | 10.8 | 9.2[b] | 168[b] | 1.6[b] | 4.3[b] |
| 1.5 | 10.8 | —[c] | 67[c] | 6.3[c,d] | 8.1[c] |

[a]Calcination at 250° C. in nitrogen, unless otherwise noted.
[b]Calcination at 400° C. in air.
[c]Calcination at 600° C. in air.
[d]XRD peaks of hydrogen tungsten oxides present.

TABLE 3

Physical Properties of WA1-TMS 14 calcined at different temperatures.

| Calcination temperature (° C.) | Bragg spacing (nm) | Surface area (m/g) | Pore size (nm) |
|---|---|---|---|
| As-synthesized | 14.0 | — | — |
| 300 | 12.1 | 130 | 6.7 |
| 400 | 10.9 | 134 | 6.7 |
| 600 | — | ~1 | — |

Synthesis of Nano-$V_2O_5$/$ZrO_2$ Using Surfactant Templating

Surfactant-templated, mesoporous vanadated zirconia with nanoparticle support was prepared by combining a 3:1 (by weight) ratio of inorganic precursors-to-organic surfactant in aqueous solution. The inorganic contribution included 1 part (by weight of total batch composition) zirconia and 0.5 part ammonium metavanadate. The zirconium oxide precursor (Zr10/20, from Nyacol Nanotechnologies, Inc.) consisted of a 20 wt % colloidal sol of 5-10 nm diameter (nominal) crystalline particles stabilized by 10 wt % nitric acid with pH 0.5. The vanadium source was ammonium metavanadate ($NH_4VO_3$, Aldrich), a yellowish-white powder sparingly soluble in water. Assuming 5 nm diameter monodisperse particles of $ZrO_2$, ammonium metavanadate loading was chosen to yield 1.5 times monolayer coverage of $V_2O_5$ on $ZrO_2$ as based on laman measurements of samples prepared using incipient wetness impregnation. The first step prepared a clear yellow solution of 0.01 molal $NH_4VO_3$ requiring several hours of stirring to reach total dissolution. The organic contribution was 0.5 part nonionic triblock polymer of average molecular formula $EO_{20}PO_{70}EO_{20}$ (Pluronic P123, BASF). Pluronic P123 was dissolved in water at concentration below 10 wt % (solubility limit).

Synthesi consisted of briefly dissolving ammonium metavanadate in an aqueous solution of 9.1 wt % Pluronic P123 (overall mixture pH ~7) under ambient conditions in open air.

Fast addition of Zr10/20 to the stirred liquid initiated immediate pH reduction to ~3 and formation of a cloudy yellow-orange solution. The solution was mixed for 2 hours and then left to quiescently age under ambient conditions overnight. Triple repetition of supernatant decant, residue wash, and centrifuge steps were followed to purify the sample. Sample was dried overnight in air then calcined at 500° C. under static air conditions for 3 hours (3° C./minute) to remove the Pluronic P123 surfactant Final black residue was ground into a fine powder.

Additional data relating to the properties of surface-templated mesostructures prepared with various precursors is given in Table 4 below.

TABLE 4

Properties of surface-templated mesostructures prepared with various precursors.[a]

| Oxide Composition | Metal Oxide Precursor | Bragg Spacing[b] (nm) | $W^{6+}/M^{n+}$ Ratio[c] |
|---|---|---|---|
| $WO_3/ZrO_2$ | Colloidal $ZrO_2$ | 11.5 | 0.31[d] |
| $WO_3/ZrO_2$ | $ZrO(NO_3)_2$ | 10.6 | 2.45 |
| $WO_3/ZrO_2$ | $ZrCl_4$ | 10.6 | 4.41 |
| $WO_3/TiO_2$ | Colloidal $TiO_2$ | 11.0 | 0.90 |
| $WO_3/Al_2O_3$ | Colloidal $Al_2O_3$ | 13.2 | 0.48 |

[a] $EO_{20}PO_{70}EO_{20}$ surface template.
[b] Before calcination.
[c] Determined through HRTEM/EDS
[d] Deviation from the bulk value (0.23) due to batch-to-batch variations.

Catalysis

We have discovered that catalysts formed according to the present techniques have unexpectedly enhanced catalytic properties, e.g. higher activities and ease in reducibility among others, that catalysts formed by conventional methods. For example, we have discovered that WZr-TMS14 has unexpectedly superior catalytic properties, as compared to conventional $WO_3/ZrO_2$ catalysts (Table 5). In particular, WZr-TMS14, sometimes referred to as nano-$WO_3/ZrO_2$, was found to be ~7 times more active (per active site on the catalyst) than the conventional material for methanol oxidation, even after accounting for the higher surface area and greater $WO_3$ content of nano-$WO_3/ZrO_2$. Calculations of the adsorption constant $K_{ads}$ and kinetic rate constant for the surface decomposition step, $k_{rds}$, showed that methanol adsorbed less on nano-$WO_3/ZrO_2$ but reacted more quickly. This suggests that there are subtle differences in the chemical environment around the active sites of the respective $WO_3/ZrO_2$ catalysts. The higher activity was also reflected in methaol TPSR experiments, in which a lower peak temperature indicated higher activity. Interestingly, using dried colloidal $ZrO_2$ for impregnation lead to a material that behaved similarly to conventional $WO_3/ZrO_2$. This indicated that not only was the nature of the $ZrO_2$ nanoparticles important to achieving the unusual catalytic properties, but that the synthesis route was also important.

TABLE 5

Kinetic data for $WO_3/ZrO_2$ prepared through impregnation of bulk $ZrO_2$ ("conventional $WO_3/ZrO_2$"), using $ZrO_2$ nanoparticles ("nano $WO_3/ZrO_2$"), and through impregnation of dried $ZrO_2$ nanoparticles ("nano $WO_3/ZrO_2$ impregnated").

| Catalyst | TOF ($s^{-1}$) At 230° C. | $T_p$ (° C.) | $E_a$ (kcal/mol) | $k_{rds}$ ($s^{-1}$) | $k_{ads}$ (L/mol) |
|---|---|---|---|---|---|
| Conventional $WO_3/ZrO_2$ | $0.77 \times 10^{-3}$ | 294 | 34.3 | 0.011 | 1.136 |
| nano-$WO_3/ZrO_2$ | $5.3 \times 10^{-3}$ | 248 | 31.4 | 0.197 | 0.437 |
| nano-$WO_3/ZrO_2$ impregnated | | 290 | 32.9 | 0.014 | |

More evidence that the $WO_3$ in nano-$WO_3/ZrO_2$ behaves differently from that in conventional $WO_3/ZrO_2$ is shown in Table 6. Under propane oxidative dehydrogenation (ODH) conditions, the $WO_3$ content of nano $WO_3/ZrO_2$ was found to reduce nearly completely, based on UV-vis measurements. The $WO_3$ was able to reduce readily because it was in polymerized form. What is surprising is that, at a calcination temperature of 600° C. and at the high $WO_3$ loading of 30 wt %, the $WO_3$ content should be crystalline and therefore should not reduce easily. The 5 wt % $WO_3$ content in conventional $WO_3/ZrO_2$ is low enough to not form $WO_3$ crystals at 500° C. and therefore remains polymerized. However, there is significantly less reduction.

TABLE 6

Relative Extents of Reduction of the $WO_3$—$ZrO_2$ Catalysts at Different Gas Compositions at 300° C.

| Catalyst | Reduction Extent | | | |
|---|---|---|---|---|
| | 1:10 $C_3H_8/O_2$ | 1:5 $C_3H_8/O_2$ | 3:1 $C_3H_8/O_2$ | 1:10 $C_3H_8/He$ |
| $5WO_3/ZrO_2$ | 5.1 | 6.8 | 15.8 | 20.9 |
| nano $WO_3/ZrO_2$ | 96.6 | 98.7 | 99.8 | 99.9 |

Without being bound by any particular theory, it is believed that the use of nanoparticles as the support material can lead to supported metal oxide catalysts if (1) the nanoparticles remain unaggregated for as long as possible during catalyst formation, (2) the supported metal oxide polymerized species is situated in the gaps between the nanoparticles, and (3) a porous catalyst nanostructure is achieved. WZr-TMS14 is merely exemplary of a larger class of nanoparticle-based supported catalysts. The nanoparticle/surfactant templating chemistry of WZr-TMS14 is a specialized method of preparation.

It is believed that any chemical method, such as sol-gel processing and precipitation, that produces nanoparticles can be modified with a second step, in which a metal salt precursor is carefully added after the nanoparticles are formed. Then either a drying technique or the addition of surfactants or other organics as pore-forming agents can give an analogous catalyst structure of polymerized metal oxide supported on nanoparticles. It is further believed that nanoparticle-based supported metal oxide materials can be prepared with more than one type of active site, leading to multifunctional catalysts, and that such a material can be the foundation upon which additional active sites can be added after catalyst structure formation.

Our data indicated that nano-$V_2O_5/ZrO_2$ reduced more easily than the conventional counterpart (Table 7), as was the case for nano-$WO_3/ZrO_2$. Whereas nano-$WO_3/Zr_2$ appeared to benefit from this for the acid-catalyzed dimethyl ether formation from methanol, this ease in reducibility did not benefit the oxidative formation of formaldehyde from methanol (as judged from methanol TPSR data, not shown). This is expected, because the active site for oxidation is the non-reduced $V_2O5$ active site. This tendency for reduction may be useful in reactions which require mild redox properties.

TABLE 7

Relative Extents of Reduction of the $V_2O_5$—$ZrO_2$ Catalysts at Different Gas Compositions

| | Reduction Extent (%) | | | |
|---|---|---|---|---|
| Catalyst | $C_3H_8/O_2 =$ 1/5 | $C_3H_8/O_2 =$ 1/1 | $C_3H_8/O_2 =$ 6/1 | 18% $C_3H_8/He$ |
| Regular $V_2O_5/ZrO_2$ | 8.2 | 19.6 | 29.9 | 50.8 |
| Nano $V_2O_5/ZrO_2$ | 22 | 38 | 45 | 69 |

Synthesis of Catalyst Using Sol-Gel Processing

A similar material can be produced by avoiding the regime of precipitation and focusing on conditions in which the $ZrO_2$ nanoparticles, vanadate precursor, and surfactant form a clear solution. Air-drying the solution at room temperature can remove the water, and force the formation of the organic-inorganic material (xerogel). Calcination removes the surfactant, to give porous nano-$V_2O_5/ZrO_2$. Alternatively, supercritical drying can be employed in place of air-drying to remove the water, resulting in the formation of an aerogel. These methods provide a direct method for controlling the supported metal oxide loading, since all the precursor components are incorporated into the structure. Nano-$MoO_3/ZrO_2$ and nano-$MoO_3/Al_2O_3$ are other examples of present effective catalysts.

Like the surfactant-templating technique, this sol-gel technique can be practiced using any desired catalytically active metal, including but not limited to vanadium, tungsten, niobium, tantalum, rhenin, and molybdenum (oxides including $WO_3$, $V_2O5$, $Nb_2O_5$, $Ta_2O_5$, $ReO_2$, $MoO_3$), any of which can be used alone or in combination with one or more of the others and metal non-oxides can be used. Precursors of the catalytic material can be salts, metal alkoxides, and organometallic complexes and mixtures of these.

In sol-gel processing, a metal alkoxide or a metal salt hydrolyzes and condenses to form nanoparticles. These nanoparticles continue to grow, and under appropriate time and synthesis conditions, can form a gel, in which the nanoparticles interconnect into a highly porous network (which imbibes the synthesis fluid). The thus-formed nanoparticles can comprise a substantially pure metal oxide, or can be a blend of metal oxides. The precursor to the supported metal (s) can be introduced as a solution of the desired metal oxide salt) after the formation of the nanoparticles, after the formation of the nanoparticle clusters, or after the formation of the nanoparticle gel network.

If a colloidal sol of nanoparticles of the desired metal oxide is used, it is preferred that the nanoparticles be between 2 and 20 nm in diameter, more preferably between 2 and 10, and still more preferably between 5 and 10 nm in diameter. Colloidal sols of such particles are commercially available.

The pore size of the compounds made using the sol-gel technique can be controlled through the use of appropriately sized porogens, or through specialized drying techniques, such as supercritical drying. Suitable porogens or pore-forming agents include cationic surfactants, anionic surfactants, zwitterionic surfactant charged polymers, charged proteins, inorganic species such as salts, and mixtures thereof. The porogen can be introduced after the formation of the nanoparticles, after the formation of the nanoparticle clusters, or after the formation of the nanoparticle gel network.

An advantage of the sol-gel technique is that the amount of catalytically active metal in the final composition can be controlled precisely because all of the catalytically active metal that is present in the initial solution remains present in the final composition. In addition to allowing precise compositional control, the sol-gel technique allows the preparation of catalyst compositions that contain levels of the catalytically active metal that are outside the concentration range at which self-assembly of nanoparticles and surfactant occurs.

In still further embodiments, the nanoparticle-based supported catalyst can be impregnated with another metal oxide or metal and/or non-surfactant polymers such as polyethylene oxide or other materials can be included in the mixture to serve as porogens.

The present invention provides new structural properties resulting from the formation of a polymerized metal oxide. In addition, enhanced reducibility of supported catalysts and new catalytic properties that have not been attainable until now are made possible with the present invention. A further advantage is the economical method of catalyst preparation, which does not require a significant change in current catalyst processing.

While preferred embodiments of this invention have been shown and described, modifications thereof can be made by one skilled in the art without departing from the spirit or teaching of this invention. The embodiments described herein are exemplary only and are not limiting. Accordingly, the scope of protection is not limited to the embodiments described herein, but is only limited by the claims which follow, the scope of which shall include all equivalents of the subject matter of the claims. The sequential ration of steps in any method claim below, without more, is not intended to require that the steps be performed in any particular order, or that any step be completed before commencement of another step.

What is claimed is:

1. A process for making a porous catalyst, comprising
   (a) providing an aqueous solution containing a nanoparticle precursor;
   (b) forming a composition containing nanoparticles;
   (c) adding a first catalytic precursor and a pore-forming agent to the composition containing nanoparticles and allowing the first catalytic precursor, the pore-forming agent, and the nanoparticles to form a solution, wherein the first catalytic precursor is a metal salt, wherein the metal salt comprises ammonium metavanadate, ammonium metatungstate, vanadium, niobium, tantalum, rhenium, rhodium, rubidium, cobalt, iron, manganese, molybdenum, or combinations thereof, and wherein the addition of the first catalytic precursor and the pore-forming agent to the composition does not result in precipitation;
   (d) air drying the solution at about room temperature so as to allow an organic-inorganic material gel structure to form; and
   (e) removing the pore-forming agent from the organic-inorganic structure so as to yield a porous catalyst.

2. The process according to claim 1, wherein the pore-forming agent is an anionic surfactant, a zwitterionic surfactant, or combinations thereof.

3. The process according to claim 1, wherein (b) and (c) are performed concurrently.

4. The process according to claim 1, wherein the nanoparticles are nanoparticles of a metal or metal oxide.

5. The process according to claim 1, wherein the porous catalyst comprises nanoparticles coated with a first catalytic component layer, wherein the first catalytic component layer is amorphous.

6. The process according to claim 1, wherein the porous catalyst comprises nanoparticles coated with a first catalytic component layer, wherein the surface density of the first catalytic component layer is greater than 4 molecules per $nm^2$.

7. The process according to claim 1, wherein the first catalytic component is non-crystalline in the porous catalyst.

8. The process according to claim 1, wherein the first catalytic precursor is at least partially polymerized in the porous catalyst.

9. The process according to claim 1, wherein the nanoparticles comprise zirconium oxide nanoparticles, titanium oxide nanoparticles, aluminum oxide nanoparticles, silicon oxide nanoparticles, or combinations thereof.

10. The process according to claim 1, wherein the pore-forming agent comprises an ethylene oxide block copolymer.

11. The process according to claim 1, wherein the pore-forming agent comprises a non-ionic poly(ethylene oxide)-poly(propylene oxide)-poly(ethylene oxide) triblock copolymer.

12. The process according to claim 11, wherein the pore-forming agent comprises $EO_{20}PO_{70}EO_{20}$, $EO_5PO_{70}EO_5$, $EO_{106}PO_{70}EO_{106}$, $EO_{17}PO_{60}EO_{17}$, or combinations thereof.

13. The process according to claim 1, wherein the pore-forming agent comprises hexadecyl trimethyl ammonium, cetyl trimethyl ammonium bromide, or combinations thereof.

14. The process according to claim 1, wherein the nanoparticles are zirconium oxide nanoparticles, the first catalytic component or precursor thereof comprises tungsten, and the pore-forming agent comprises $EO_{20}PO_{70}EO_{20}$, $EO_5PO_{70}EO_5$, $EO_{106}PO_{70}EO_{106}$, $EO_{17}PO_{60}EO_{17}$, or combinations thereof.

15. The process according to claim 1, wherein the nanoparticles are zirconium oxide nanoparticles or aluminum oxide nanoparticles, the first catalytic precursor comprises tungsten or vanadium, and the pore-forming agent comprises $EO_{20}PO_{70}EO_{20}$, $EO_5PO_{70}EO_5$, $EO_{106}PO_{70}EO_{106}$, $EO_{17}PO_{60}EO_{17}$, or combinations thereof.

16. The process according to claim 1, wherein (e) comprises calcining the organic-inorganic structure to remove the pore-forming agent.

17. The method of claim 1 further comprising impregnating the porous catalyst with a second catalytic precursor, a non-surfactant polymer, or combinations thereof.

18. The process according to claim 1, wherein the gel is formed by hydrolyzing and condensing a metal alkoxide, a metal salt, or combinations thereof.

19. A process comprising:
  forming a gel comprising a plurality of nanoparticles, wherein at least some of the nanoparticles have a diameter of two nanometers;
  adding a catalyst precursor to the gel, wherein the catalyst precursor is a metal salt and wherein the metal salt comprises ammonium metavanadate, ammonium metatungstate, vanadium, niobium, tantalum, rhenium, rhodium, rubidium, cobalt, iron, manganese, molybdenum, or combinations thereof;
  adding a porogen to the gel, wherein the porogen is anionic or zwitterionic and wherein the addition of the porogen to the catalyst precursor does not result in precipitation;
  drying the gel, the catalyst precursor, and the porogen, thereby forming a dried gel; and
  removing the porogen from the dried gel, thereby forming a porous catalyst.

20. A process comprising:
  forming a gel comprising a plurality of nanoparticles;
  adding a catalyst precursor to the gel, wherein the catalyst precursor is a metal salt and wherein the metal salt comprises ammonium metavanadate, ammonium metatungstate, vanadium, niobium, tantalum, rhenium, rhodium, rubidium, cobalt, iron, manganese, molybdenum, or combinations thereof;
  adding a porogen to the gel, wherein the porogen is anionic and wherein the addition of the porogen to the catalyst precursor does not result in precipitation;
  drying the gel, the catalyst precursor, and the porogen, thereby forming a dried gel; and
  removing the porogen from the dried gel, thereby forming a porous catalyst.

21. The process according to claim 20, wherein at least some of the nanoparticles have a diameter of two nanometers.

22. The process according to claim 20, wherein the gel is formed by hydrolyzing and condensing a metal alkoxide, a metal salt, or combinations thereof.

* * * * *